United States Patent [19]  [11] Patent Number: 4,950,284
Green et al.  [45] Date of Patent: Aug. 21, 1990

[54] FASCIA CLIP

[75] Inventors: David T. Green, Westport; Keith Ratcliff, Sandy Hook, both of Conn.

[73] Assignee: United States Surgical Corporation, Norwalk, Conn.

[21] Appl. No.: 421,278

[22] Filed: Oct. 13, 1989

Related U.S. Application Data

[63] Continuation-in-part of Ser. No. 116,627, Nov. 3, 1989, abandoned.

[51] Int. Cl.⁵ ............................................. A61B 17/00
[52] U.S. Cl. ..................................... 606/216; 606/151; 606/220; 24/706.3; 24/707.6
[58] Field of Search ....................... 606/151, 216, 220; 24/16 PB, 30.5 F, 150 FP, 155 R

[56] References Cited

U.S. PATENT DOCUMENTS

| | | | |
|---|---|---|---|
| 672,159 | 4/1901 | Bechtold | 24/710.7 |
| 3,167,072 | 1/1965 | Stone et al. | 604/179 |
| 3,570,497 | 3/1971 | Lemole | 606/151 |
| 3,650,274 | 3/1972 | Edwards et al. | 606/223 |
| 3,926,193 | 12/1975 | Hasson | 606/218 |
| 4,390,019 | 6/1983 | LeVeen et al. | 606/158 |
| 4,535,764 | 8/1985 | Ebert | 24/23 EE |
| 4,730,615 | 3/1988 | Sutherland | 606/215 |

Primary Examiner—Randall L. Green
Assistant Examiner—Gary Jackson
Attorney, Agent, or Firm—Kenyon & Kenyon

[57] ABSTRACT

The fascia clip is of two-piece construction having an elongated base and a flexible strap. The base is sized to bridge over an incision in fascia tissue and has openings at opposite ends. The strap has a pointed distal end for passage through the opening at the proximal end of the base so as to pierce through the fascia tissue. After being directed under the incision, the strap can again pierce the tissue to pass through the opening at the distal end of the base in order to be gripped therein. The strap has an enlarged head at the proximal end to prevent complete passage through the opening at the proximal end of the base. In one embodiment, resilient teeth are used at the distal end of the strap to engage with a web about the opening at the distal end of the base. In another embodiment, a resilient tab on the enlarged head of the base engages in an opening in the distal end of the strap.

36 Claims, 6 Drawing Sheets

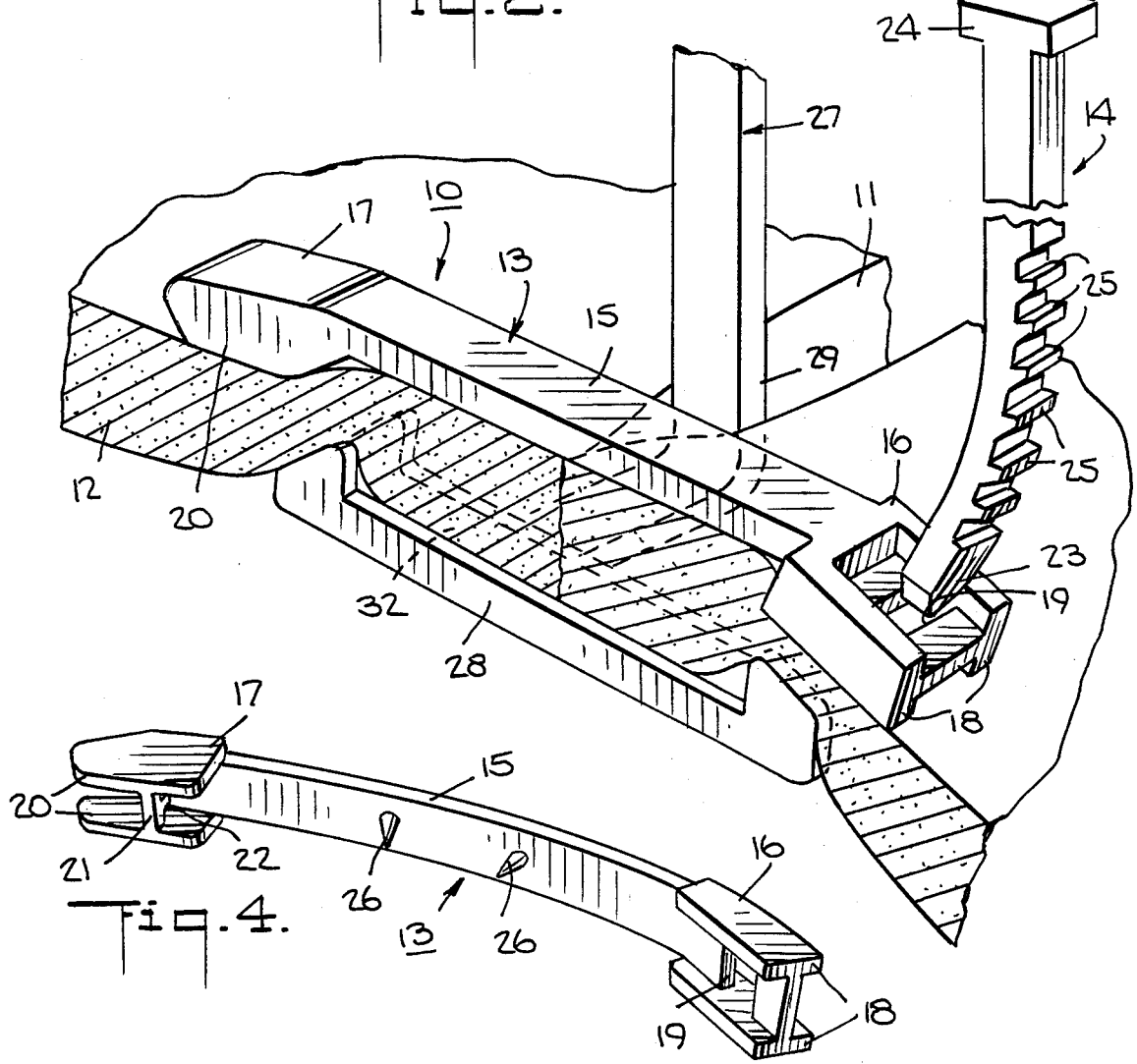
Fig. 2.
Fig. 4.
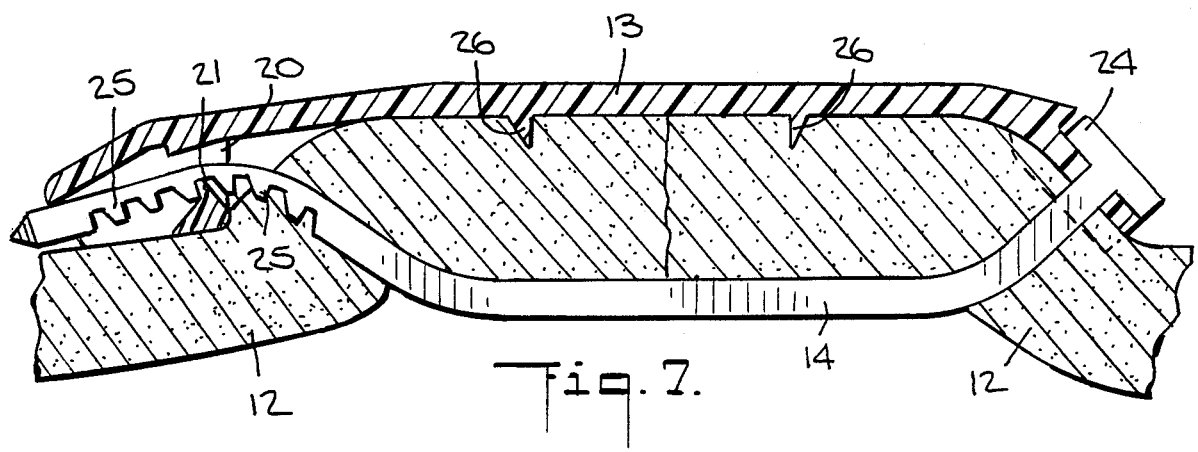
Fig. 7.

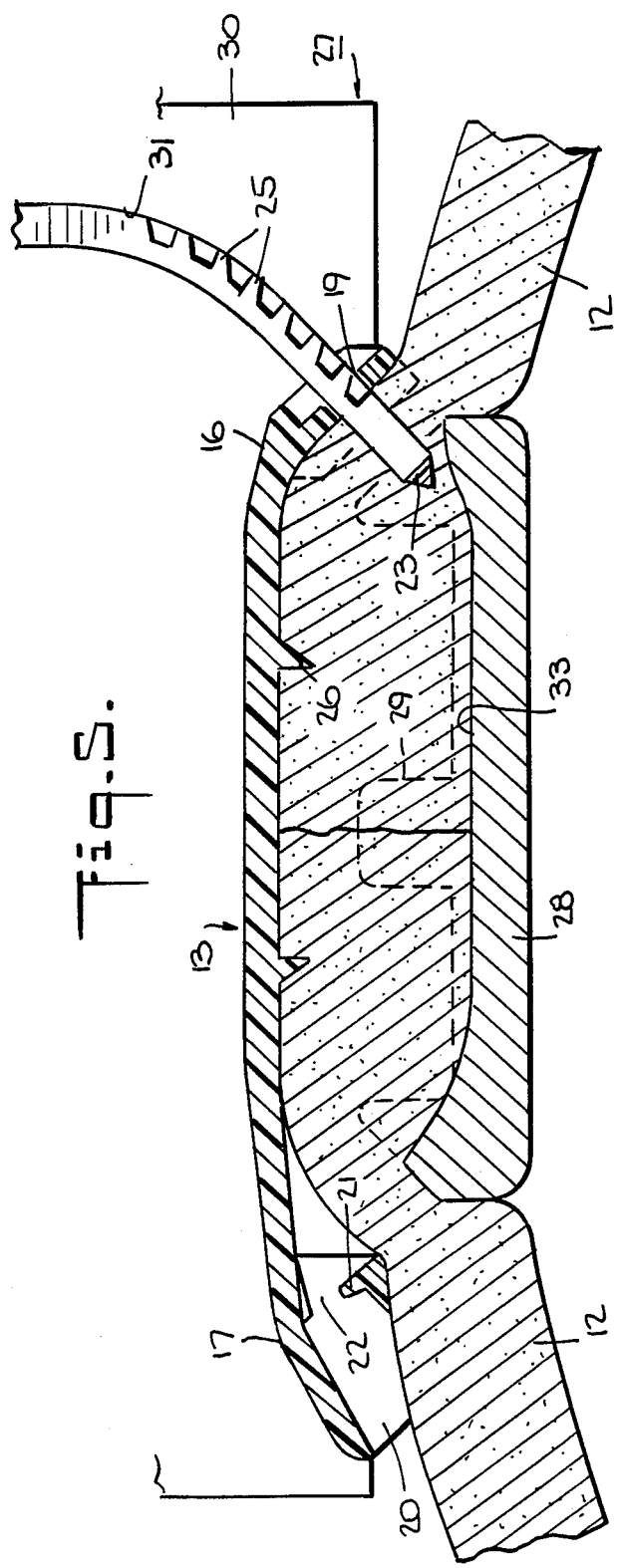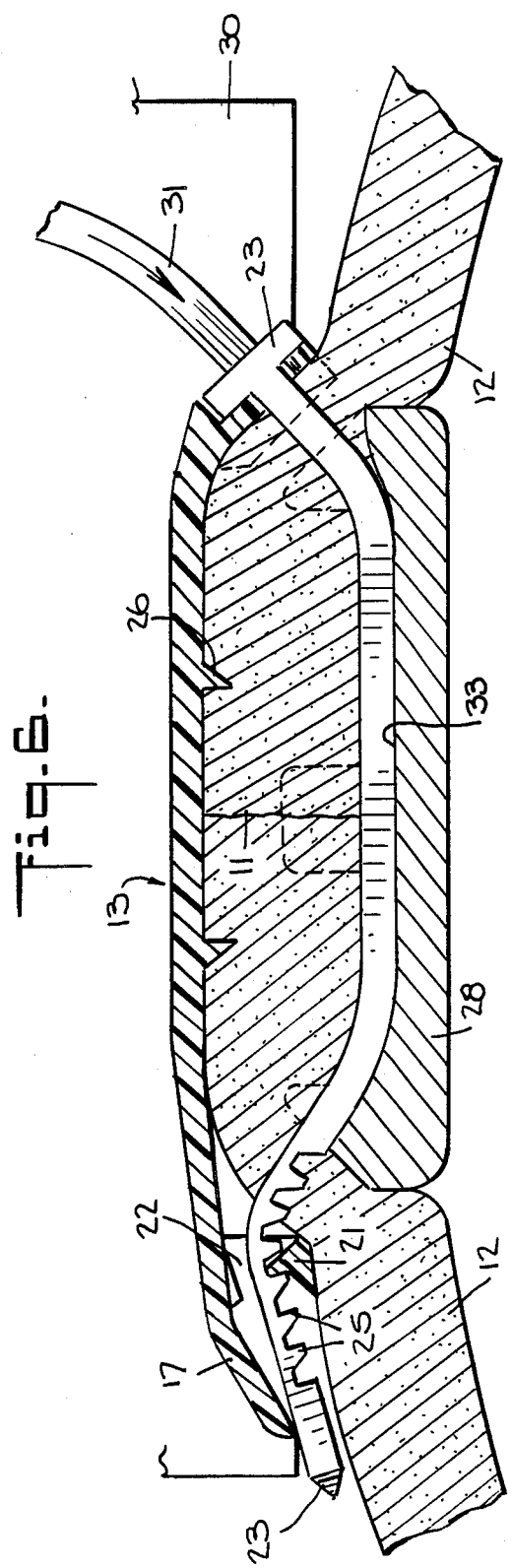

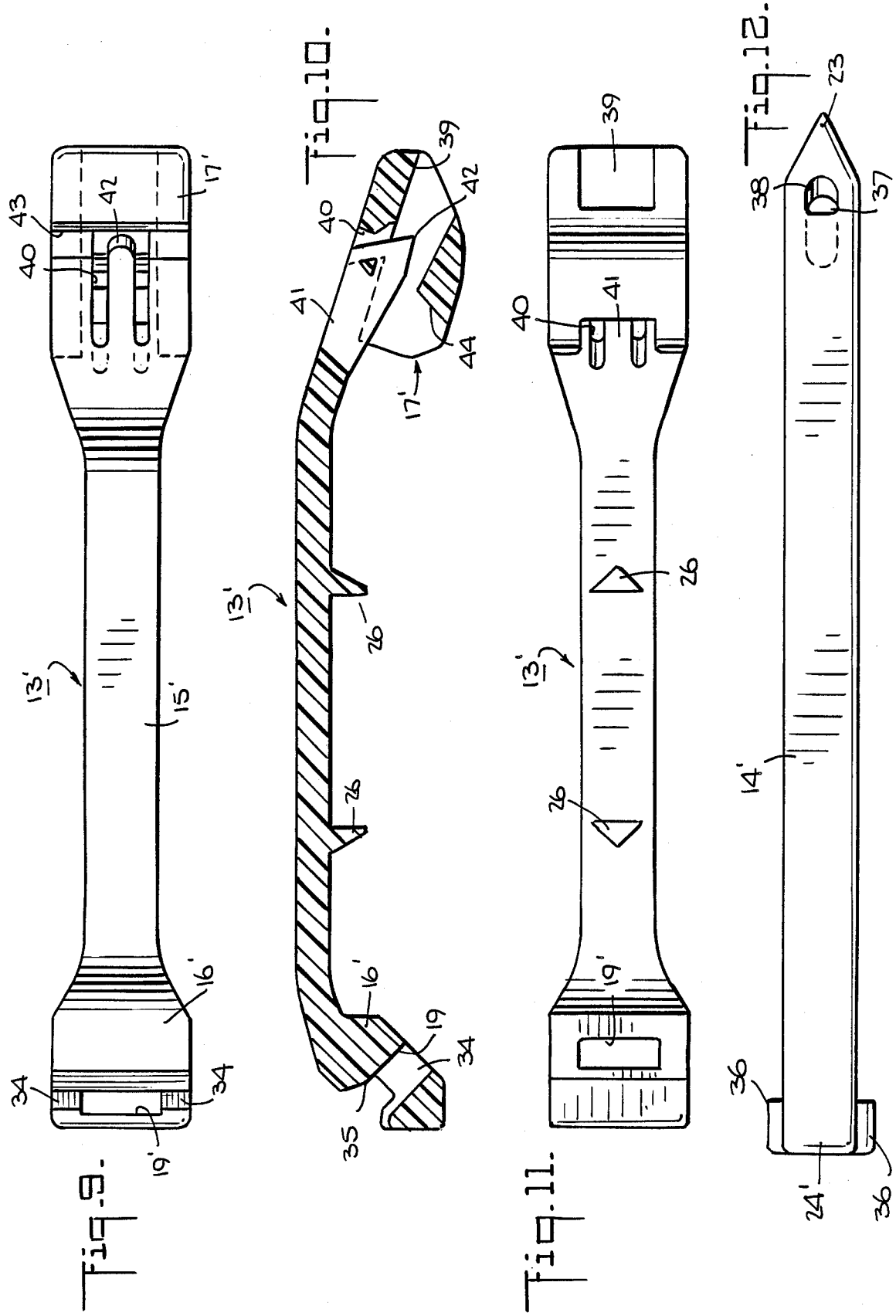

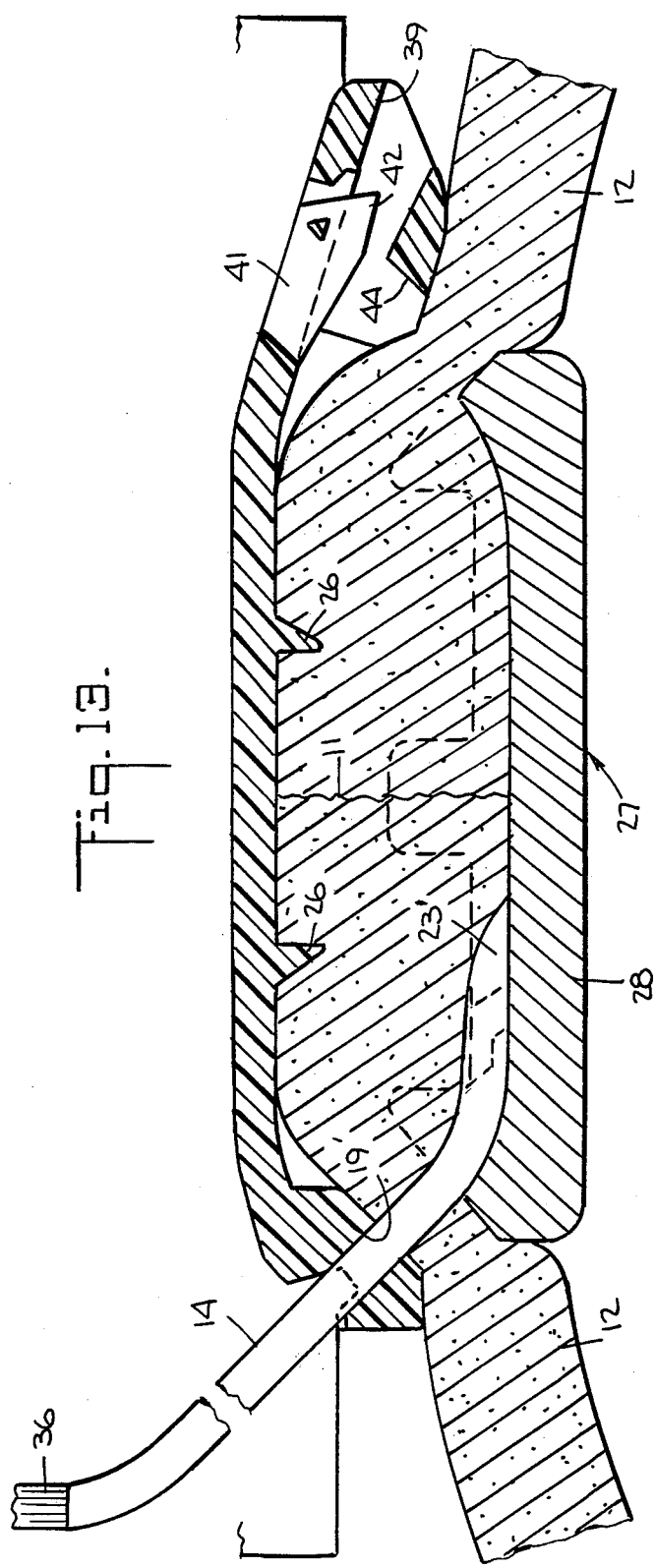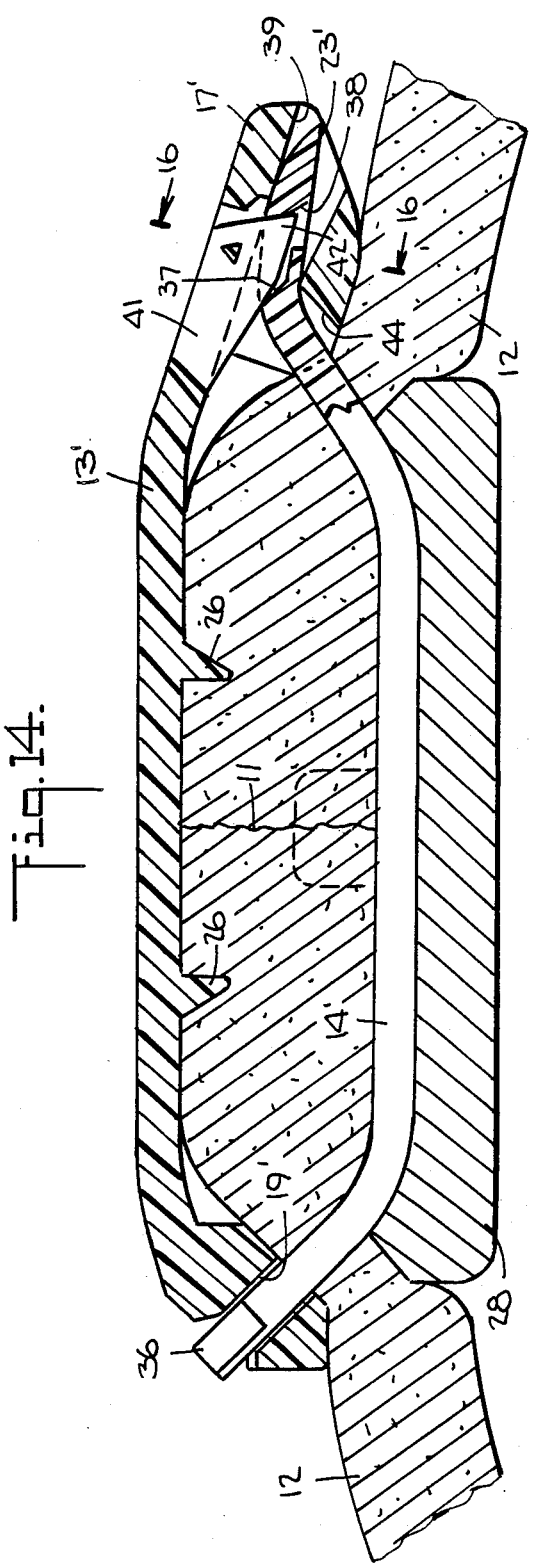

FASCIA CLIP

This is a continuation-in-part of Ser. No. 116,627 and filed Nov. 3, 1987 now abandoned.

This invention relates to a fascia clip.

Heretofore, various advances have been made over the years in the closing of incisions in various types of surgical operations. For example, the use of stapling instruments for stapling various types of incisions and openings has become prevalent in order to reduce the time of closure for a surgical procedure. However, the use of stapling instruments has not been entirely suitable for all types of closures. In addition, as is known, fascia tissue is relatively thick and is not easily manipulated for suturing using conventional suturing techniques. Further, fascia tissue takes a relatively long time to sew or suture and has such little strength that sutures can pull out relatively easily.

Accordingly, it is an object of the invention to provide for a rapid closure of an incision in fascia tissue.

It is another object of the invention to provide a relatively simple clip for closing of fascia tissue.

It is another object of the invention to be able to close an incision in fascia tissue in a reliable manner.

Briefly, the invention provides a fascia clip of two-piece construction which is comprised of a base and a flexible strap.

The base of the fascia clip is constructed of an elongated shape with an opening at a proximal end and a gripping means at the distal end for gripping a distal end of the strap. The flexible strap is constructed with a pointed distal end which is sized for passage through the opening of the base while being provided with means at the distal end for engaging with the gripping means of the base to prevent withdrawal of the distal end of the strap from the distal end of the base. In addition, the proximal end of the strap is made of greater size than the opening in the proximal end of the base in order to prevent passage of the proximal end of the strap through the base.

When in use, the base of the clip is positioned across an incision in a layer of fascia tissue. Thereafter, the strap is pushed through the opening in the proximal end of the base to pierce through the fascia tissue. The pointed tip is then guided to pass under the incision and again pierce through the fascia tissue to enter into the gripping means at the distal end of the base with the enlarged proximal end of the strap preventing passage through the opening at the proximal end of the base.

In one embodiment, the gripping means of the base may be in the form of a slot or opening while the strap may have a means in the form of a plurality of teeth for selectively engaging about the opening.

In addition, the base may be provided with an anchoring means, for example, in the form of projections to penetrate into the fascia tissue on both sides of an incision to prevent slippage of the base during and after a closing operation.

In another embodiment, the gripping means may include a resilient tab integral with the remainder of the base and projecting into a passage through an enlarged proximal end of the base. In this embodiment, the distal end of the strap is provided with an aperture for receiving a distal end of the tab. In order to enhance the gripping effect, the tab is provided with a wedge-shaped tip which projects into the aperture of the strip in order to prevent withdrawal of the distal end of the strap from the passage in the base.

In order to close an incision, a plurality of fascia clips would be used to close a substantial portion of the incision. When the instrument used to guide the individual straps from one opening to the other opening of a base can no longer be utilized, the remainder of the incision would be sewn or sutured using conventional techniques.

The fascia clip is made of any suitable material such as Nylon, Dacron or polyamide, and polyester respectively and polypropylene and may also be made of absorbable material.

These and other objects and advantages of the invention will become more apparent from the following detailed description taken in conjunction with the accompanying drawings wherein:

FIG. 2 illustrates a perspective view of a fascia clip immediately prior to insertion of a strap in the base of the clip in accordance with the invention;

FIG. 4 illustrates a perspective view of a base of a fascia clip in accordance with the invention;

FIG. 5 illustrates a part cross-sectional view of a fascia clip during initial piercing of the strap into the fascia tissue;

FIG. 6 illustrates a view similar to FIG. 5 of a fascia clip in a closed position;

FIG. 7 illustrates a cross-sectional view of a closed incision in accordance with the invention;

FIG. 9 illustrates a plan view of a base of the fascia clip of FIG. 8;

FIG. 10 illustrates a side view of the base of the fascia clip of FIG. 8;

FIG. 11 illustrates a bottom view of the base of the fascia clip of FIG. 8;

FIG. 12 illustrates a plan view of the strap of the fascia clip of FIG. 8;

FIG. 13 illustrates a part cross-sectional view of the fascia clip of FIG. 8 during initial piercing of the strap into the fascia tissue in accordance with the invention;

FIG. 14 illustrates a view similar to FIG. 13 of the fascia clip in a closed position;

Figure 1:
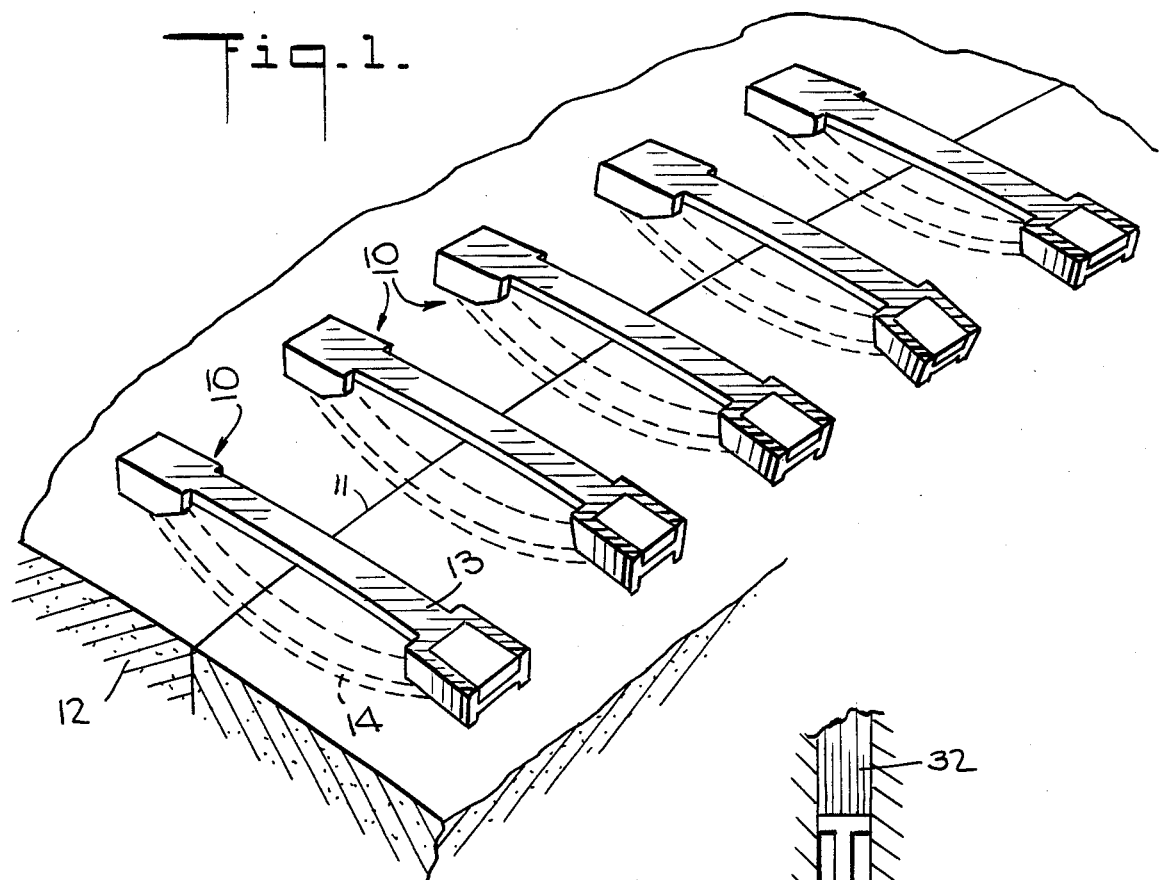
FIG. 1 illustrates a perspective view of a plurality of fascia clips closing a portion of an incision in accordance with the invention.

Referring to FIG. 1, a plurality of fascia clips 10 are used to close at least a major portion of an incision 11 within a layer of fascia tissue 12. As indicated, each clip 10 is of two-piece construction being formed of a base 13 and a strap 14.

Referring to FIGS. 1 and 2, each base 13 is of elongated shape and is made of a resilient material which is suitable for use in a patient and which may be absorbable. Each base 13 also has a main body portion 15, an enlarged proximal end 16, which may extend angularly from the main body portion 15 and an enlarged distal end 17 which may extend outwardly of the main body portion 15. The enlarged proximal end 16 can be formed by a pair of parallel flanges 18 and includes an opening 19 for passage of a strap 14. The enlarged distal end 17 includes a gripping means in the form of a pair of parallel flanges 20 which extend transversely of the main body portion 15 and a web 21 (see FIG. 4) which extends between and in perpendicular relation to the flanges 20 to form an opening or slot 22 (FIG. 4) which is sized for passage of a strap 14.

Referring to FIG. 2, each strap 14 is of resilient and flexible material and has a pointed distal end 23 which is sized for passage through the openings 19, 22 (FIG. 4) of a base 13. In addition, the strap 14 is provided with a proximal end 24 of greater size than the opening 19 in the proximal end of the base 13 in order to prevent passage of the proximal end 24 through the opening 19. The remainder of the strap 14 is of suitable cross-section, such as rectangular, and tapers to the pointed distal end 23. In this respect, the pointed distal end 23 is shaped so as to be able to pierce the fascia tissue 12 under a suitable force. For example, the distal end 23 may taper along the top and bottom surfaces, as viewed in FIG. 7, on a first angle of 45~ while two side surfaces taper on a second angle to produce a sharp point for piercing.

Each strap 14 is also provided with means in the form of resilient teeth 25 at the distal end for engaging with the distal end 17 of the base in order to prevent withdrawal of the distal end of the strap from the opening 22 in the base at the distal end. In this respect, the flanges 17 and web 21 at the distal end of the base 13 provides a gripping means for gripping the distal end of the strap 14 as indicated in FIG. 7. A plurality of teeth may be provided to permit the clip to automatically adjust to varying thicknesses of tissue.

Each base 13 also has an anchoring means in the form of a pair of projections or pins 26 which are shaped and sized to penetrate into the fascia tissue 12 on both sides of the incision 11 to prevent slippage of the base 13 as well as to prevent separation of the abutted tissue. As indicated, the projections 26 are positioned intermediately of the ends 16, 17 and near the center of the base 13.

Referring to FIG. 1, in order to close the incision 11 in the fascia tissue 12, a multiplicity of clips 10 are utilized. In this respect, the base 13 for each clip 10 is initially placed transversely over the incision 11 with the projections 26 penetrating into the tissue 12 to hold the tissue 12 and the base 13 in place. Thereafter, the strap 14 is passed through the opening 19 in the proximal end of the base 13 as indicated in FIG. 2. After piercing through the fascia tissue 12, the strap 14 is guided underneath the incision 11 and then directed upwardly to again pierce the fascia tissue 12 and pass through the opening or slot 22 (see FIGS. 3, 4 and 5) at the distal end of the base 13. The resilient teeth 25 pass through the slot 22, more or less, so that the distal end of the strap 14 is gripped within the distal end of the base 13 in a secure manner. It is preferable that the pointed distal end 23 not protrude beyond the distal end of the base. As indicated in FIG. 7, the teeth 25 of the strap 14 are spaced apart a distance greater than the thickness of the web 21 and are angled toward the rear or proximal end with a flat or perpendicular flank for abutting against the web 21.

Figure 3:
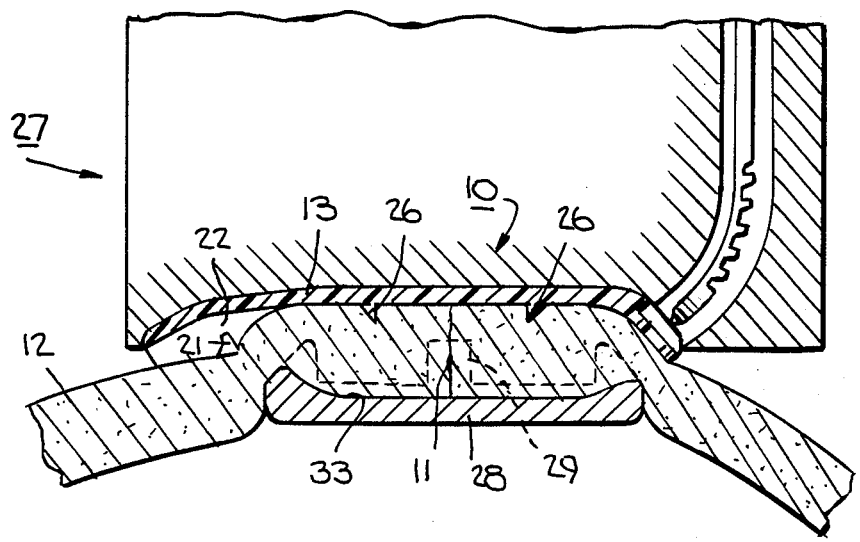
FIG. 3 illustrates a view of an apparatus for applying a fascia clip into a layer of fascia tissue in accordance with the invention.

Referring to FIGS. 2 and 3, an instrument 27 which is suitable for affixing a clip 10 in place includes an anvil or guide 28 which is mounted on a support rod 29 from a housing 30. In addition, the housing 30 includes a guide passage 31 (see FIG. 3) which receives a strap 14 and a plunger 32 for expelling the strap 14 from the passage 31. The plunger 32 may be actuated by any suitable means (not shown) so as to slide forwardly within the guide passage 31 and, subsequently, returned to an initial position.

As indicated in FIG. 3, the guide passage 31 is of curved-shaped at the lower end, as viewed, such that the strap 14 can be expelled angularly from the housing 30 as the plunger 32 moves downwardly. To this end, the strap 14 is sufficiently resilient to follow the contour of the guide passage 31. Further, the strap 14 is of sufficient strength to resist buckling under the force produced by the plunger 32.

Referring to FIG. 2, the anvil or guide 28 is of elongated shape so as to bridge over the incision 11 in the fascia tissue 12. In addition, the anvil 28 preferably has an internal groove or channel 33 (see FIG. 3) of a size substantially equal to the width of the strap 14 in order to guide the strap 14 under the incision 11 and subsequently upwardly, as viewed, into the distal end of the base 13. To this end, as indicated in FIGS. 5 and 6, the groove 33 has a substantially flat central portion with curved or angular inlet and outlet portions.

The rod 29 is of L-shape as indicated in FIG. 2 to permit the anvil 28 to be fitted under the section of the incision 11 which is to be clipped without interfering with the clipping operation.

When using the instrument 27, the anvil 28 is first inserted into the incision 11, for example, side-ways, and then rotated 90~ and located under the section of the tissue 12 which is to be clipped, i.e., near one end of the incision 11.

Further, the instrument 27 may be constructed to clamp the tissue 12 so as to approximate the incision 11 and thereafter hold the base 13 fixed for passage of a strap 14 therethrough.

Next, the base 13 for a clip 10 is positioned transversely over the incision 11 in alignment with the anvil 28 with the projections 26 penetrating into the tissue 12. In this respect, the instrument 27 may be provided with a suitable holder or magazine from which a series of bases 13 and straps 14 may be delivered individually, for example, from the housing 30 in an automatic sense.

Next, with a strap 14 within the guide passage 31, the plunger 32 is actuated so that the strap 14 is expelled from the guide passage 31 as indicated in FIGS. 3 and 5 to pass through the opening 19 at the proximal end of the base 13. At the same time, the pointed distal end 23 of the strap 14 pierces through the fascia tissue 12 (see FIG. 5) and slides into the groove 33 of the anvil 28. Continued motion of the strap 14 from the guide passage 31 causes the strap to slide along and within the groove 33 of the anvil 28 until being deflected upwardly at the exit end of the groove 33 to again pierce the fascia tissue 12 on the opposite side of the incision 11 (see FIG. 6). The pointed distal end 23 of the strap 14 again pierces the tissue 12 and passes through the slotted opening 22 at the distal end of the base 13. Motion of the strap 14 continues until the enlarged head 24 abuts against the proximal end of the base 13. As indicated in FIGS. 1 and 6, the proximal end of the base 13 is recessed to receive the enlarged head 24 of the strap 14 in a flush manner.

As indicated in FIG. 6, when the enlarged head 24 of the strap 14 has abutted the proximal end of the base 13, the teeth 25 at the distal end of the strap 14 have passed into and through the opening 22 at the distal end 17 of the base 13 with the back of one of the teeth 25 engaging the web 21. In this manner, the distal end of the strap 14 is gripped at the distal end of the base 13. If a plurality of teeth 25 are present, the thickness of the tissue will determine which tooth will engage the web 21.

Each strap 14 may alternatively be provided with teeth or the like along the sidewalls at the distal end in order to pass through the slot 22 and to engage with the walls of the web 21 defining the slot 22. In this case a pair of teeth would abut against the wall 21 after being flexed to pass through the slot 22. In either case, it is preferable to have the teeth spaced such that the tip 23 remains covered by the distal end 17 of the base 10 when the clip is formed.

After each ejection of a strap 14 from the housing 29, the apparatus 26 is moved to a new position along the incision 11 for application of a subsequent clip 10. After a series of clips 10 have been put in place as indicated in FIG. 1, and before the incision is completely closed, the instrument 26 is removed so that the remainder of the incision can be sewn or sutured, for example, in a conventional manner. Of note, the remaining portion of the incision 11 which requires such conventional suturing is a minor fraction of the overall incision 11. That is, the unclipped length of the incision should be sufficient to permit ready removal of the instrument 27 after having closed a major portion of the incision 11.

Figure 8:
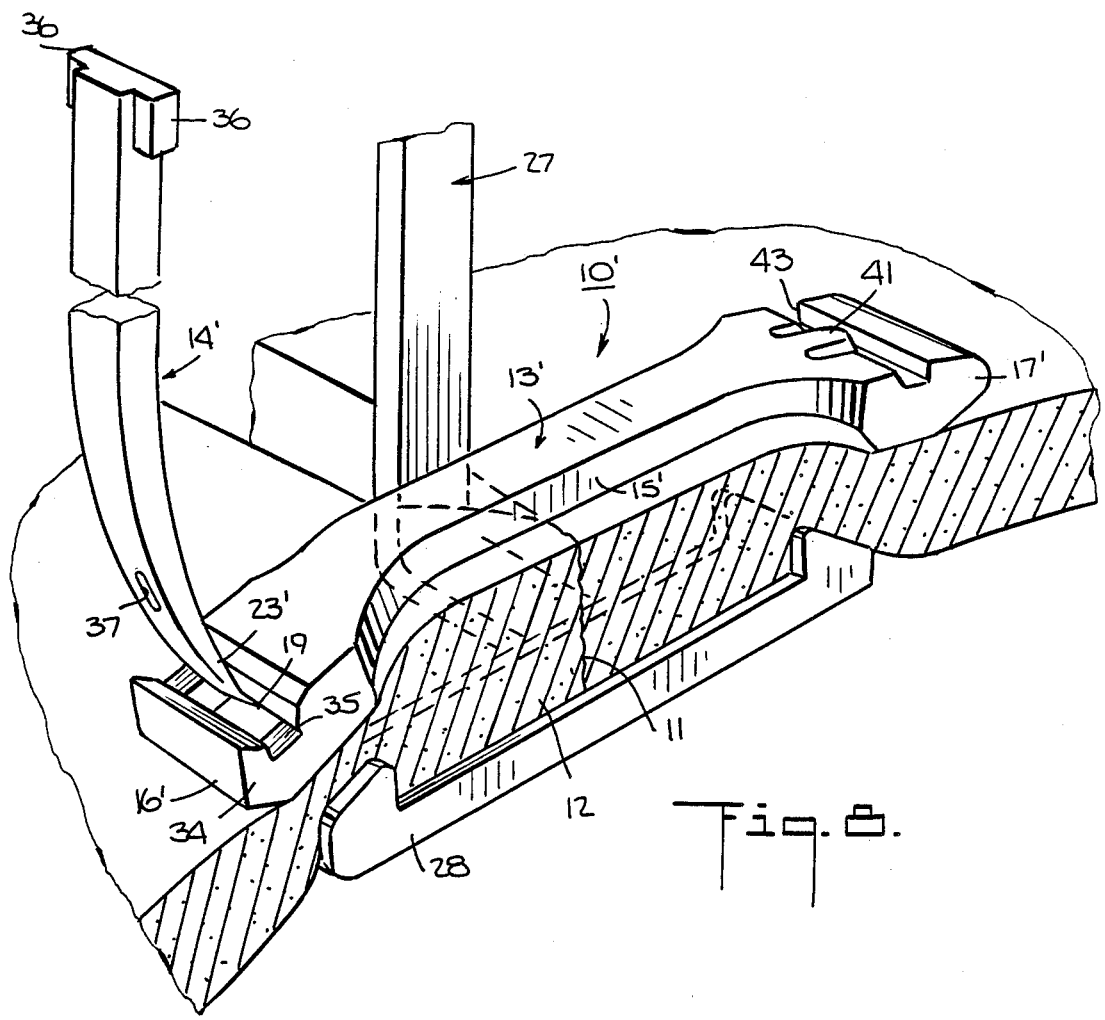
FIG. 8 illustrates a perspective view of a modified fascia clip closing a portion of an incision in accordance with the invention.
Figure 15:
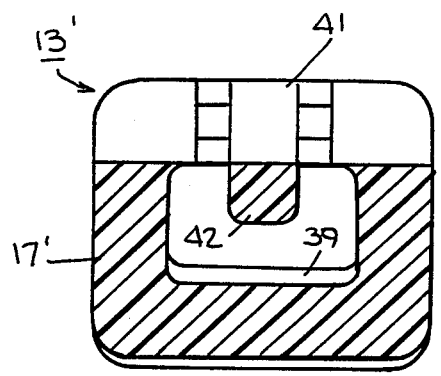
FIG. 15 illustrates a cross-sectional view of the distal end of the base of the fascia clip of FIG. 8.
Figure 16:
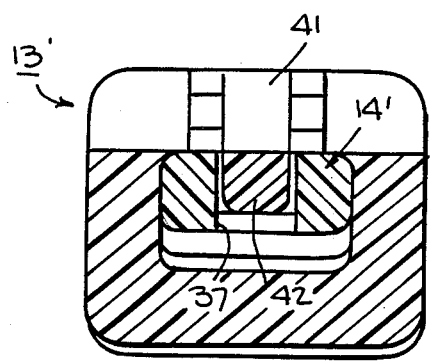
FIG. 16 illustrates a view taken on line 16—16 of FIG. 14.

Referring to FIG. 8, wherein like reference characters indicate like parts as above, the fascia clip 10', as above, includes a base 13, and a strap 14'. The base 13' is of elongated shape and has a main body portion 15' and enlarged proximal end 16' which extends angularly from the main body portion 15' and an enlarged distal end 17' which may extend outwardly of the main body portion 15.

Referring to FIGS. 9 and 10, the proximal end 16' of the base 13' includes an opening 19' for passage of the strap 14'. In addition, each side wall 34 defining the opening 19' is provided with a recess 35 for purposes as described below. As indicated in FIG. 10, each recess 35 is located on an axis out of alignment with the axis of the opening 19'. That is, each recess 35 terminates distally of the end wall of the opening 19'.

Referring to FIG. 12, the strap 14' has a pointed distal end 23' and an enlarged proximal end 24'. In this respect, the proximal end 24' is provided with a pair of laterally extending flanges 36 which are sized to fit into the recesses 35 of the base 13' (see FIG. 14). In addition, the distal end 23' is provided with an aperture 37. As indicated in FIG. 12, the aperture 37 has a smaller opening on one side than on the opposite side of the strap 14'. In addition, the distal wall 38 defining the aperture 37 slopes proximally from top to bottom as viewed in FIG. 12. The shape of the aperture 37 is more particularly illustrated in FIG. 14.

Referring to FIGS. 9 and 10, the enlarged distal end 17' of the base 13' is formed with a longitudinal passage 39 which is sized, as indicated in FIG. 14, to receive the distal end 23' of the strap 14' as well as with an aperture 40 which communicates transversely with the passage 39. In addition, a resilient tab 41 extends longitudinally of the opening 40 with a wedge shape tip 42 extending into the passage 39. This tab 41 serves as a gripping means for the distal end 23' of the strap 14' and as indicated in FIGS. 9 and 10, extends integrally from the remainder of the base 13'.

As indicated in FIGS. 8 and 9, the enlarged distal end 17' of the base 13' is provided with a slot 43 which extends transversely across the width of the distal end 17' such that the resilient tab 41 projects slightly into the slot 43.

Referring to FIG. 10, the distal end 17' of the base 13' has a flat surface 44 leading to the passage 39 in angular relation in order to define a ramp for the distal end of the strap 14' for entry into the passage 39 (see FIG. 14).

Referring to FIG. 8, in order to close the incision in fascia tissue 12, a multiplicity of clips 10' are utilized. As above, the base 13' for each clip 10' is initially placed transversely over the incision 11 with the projections 26 penetrating into the tissue 12 to hold the tissue 12 and base 13' in place. Thereafter, the pointed distal end 23' of the strap 14' is passed through the opening 19' in the proximal end of the base 13'. As indicated the flanges 36 at the proximal end of the strap 14 are on the top side whereas the enlarged part of the opening 37 is on the bottom side.

Referring to FIG. 13, after piercing through the fascia tissue 12, the distal end 23' of the strap 14' is guided underneath the incision 11 via the guide 28 of the affixing instrument 27 and then directed upwardly to again pierce the tissue 12 and to pass into the passage 39 at the distal end 17' of the base 13'. During this time, the pointed distal end 23' of the strap 14' is guided by the ramp 44 on the base 13' into the passage 39. In addition, the resilient tab 41 is flexed upwardly, as viewed in FIG. 14, under the force of the distal end 23, of the strap 14'. As the aperture 37 of the strap 14' comes into alignment with the tab 41, the tab 41 snaps into the opening 37 of the strap 14'. As illustrated in FIG. 14, the wedge-shaped tip 42 of the tab 41 engages against the sloped wall 38 of the opening 37 in wedge like manner. In this position, the tab 41 serves to prevent withdrawal of the distal end 23' of the strap 14' from the passage 39 in the proximal direction. Thus, the greater the force to withdraw the strap 14' from the passage 39 the greater the force on the tab 41 and thus the greater the wedging action of the tab 41.

As indicated in FIG. 14, once the strap 14' has been snap-fitted into gripping engagement with the base 13', the distal end 23' of the strap 14' remains in a recessed manner within the passage 39 of the base 13'.

One advantage of the fascia clip 10' of FIG. 8 relative to the fascia clip 10 of FIG. 1 resides in a use of a compression fit arrangement for the gripping means at the distal ends of the base 13' and strap 14'. In the embodiment of FIG. 1, it is possible that the interference fit type gripping means may become loose due to the engaging teeth becoming round overtime and sliding on the engaging surfaces. With the compression fit provided by the tab 41 of the embodiment of FIG. 8, no rounding effect occurs.

Since the absorption rate of the material may deteriorate over time, the compression fit provided by the gripping means of the embodiment of FIG. 8 provides a better mechanical fit.

The invention thus provides a fascia clip which can be readily used to close an incision in fascia tissue. In this respect, the force required to pierce the fascia tissue can be developed through an instrument which is able to readily push the pointed strap through the tissue in a minimum of time and with a minimum of manual effort.

Further, the invention provides a fascia clip which can also be made of absorbable material particularly where the clip is to be reabsorbed by the body.

The invention further provides a fascia clip which can be readily adapted to surgical instruments for rapid closing of incisions in fascia tissue.

The invention also provides a fastener which will not pull out of the fascia tissue as easily as a suture.

What is claimed is:

1. A fascia clip comprising
    a base of elongated shape having a main body portion, a transverse opening at one end and gripping means at an opposite end; and
    a flexible strap of solid cross-section having a pointed distal end sized for passage through said opening of said base and for gripping in said gripping means, a proximal end of greater size than said opening and an intermediate portion in spaced parallel relation to said main body portion to contain tissue therebetween.

2. A fascia clip as set forth in claim 1 wherein said base and said strap are made of absorbable material.

3. A fascia clip as set forth in claim 1 wherein said base and said clip are made of a material selected from the group consisting of polyamide, polyester and polypropylene.

4. A fascia clip as set forth in claim 1 wherein said proximal end of said strap has as enlarged head for abutting said one end of said base.

5. A fascia clip as set forth in claim 4 wherein said head of said strap has a rectangular profile.

6. A fascia clip as set forth in claim 5 wherein said gripping means includes a slot for passage of said distal end of said strap therethrough and said strap includes a plurality of teeth at said distal end for selectivity engaging with said base about said slot.

7. A fascia clip as set forth in claim 6 wherein said base and said strap are made of absorbable material.

8. A fascia clip as set forth in claim 1 wherein said gripping means includes a resilient tab and said distal end of said strap has an aperture receiving a distal end of said tab therein.

9. A fascia clip as set forth in claim 8 wherein said tab has a wedge-shaped tip projecting into said aperture of said strap.

10. A fascia clip as set forth in claim 8 wherein said opposite end of said base is enlarged and includes a longitudinal passage receiving said distal end of said strap and said tab is received in said aperture of said strap with the length of said passage.

11. A fascia clip comprising
    a base of elongated shape having a first opening at a distal end and a second transverse opening at a proximal end; and
    a resilient strap having a distal end sized for passage through said second opening and said first opening of said base, a proximal end of greater size than said second opening to prevent passage of said proximal end through said second opening and means at said distal end for engaging with said base to prevent withdrawal of said distal end of said strap from said first opening of said base.

12. A fascia clip as set forth in claim 11 wherein said base and said strap are made of absorbable material.

13. A fascia clip as set forth in claim 11 wherein said strap is of rectangular cross-section.

14. A fascia clip as set forth in claim 11 wherein said proximal end of said strap has an enlarged head for abutting said proximal end of said base.

15. A fascia clip as set forth in claim 11 wherein said base has a main body portion and said proximal end of said base extends angularly from said main body portion.

16. A fascia clip as set forth in claim 15 wherein said distal end of said base extends outwardly of said main body portion.

17. A fascia clip as set forth in claim 15 wherein said base includes a pair of projections for penetrating into fascia tissue to anchor said base in place.

18. A fascia clip comprising
    a base of elongated shape having a main body portion, a proximal end extending angularly from said main body portion and having a first opening therein, and a distal end extending outwardly of said main body portion and having a second opening therein; and
    a strap of rectangular cross-section having a distal end sized for passage through said first opening and said second opening of said base, a proximal end of greater size than said first opening to prevent passage of said proximal end through said first opening and means at said distal end for engaging with said base to prevent withdrawal said distal end of said strap from said second opening of said base.

19. A fascia clip as set for in claim 18 wherein said base and said strap are made of absorbable material.

20. A fascia clip as set forth in claim 18 wherein said distal end of said base includes a pair of parallel flanges extending transversely of said main body portion and a web extending between and perpendicular to said flanges, said web having said second opening therein.

21. A fascia clip as set forth in claim 20 wherein said means includes a plurality of resilient teeth.

22. A fascia clip as set forth in claim 21 wherein said strap has a pointed distal end for piercing tissue.

23. A fascia clip comprising
    a base of elongated shape having a main body portion and a transverse opening at one end of said body portion;
    a flexible strap having a pointed distal end sized for passage through said opening of said base, an intermediate portion opposite said main body portion to contain tissue therebetween and a proximal end of greater size than said opening; and
    gripping means for gripping said distal end of said strap at a distal end of said base to prevent withdrawal of said distal end of said one strap from said base.

24. A fascia clip as set forth in claim 23 wherein said gripping means includes a slot for passage of said distal end of said strap therethrough and said strap includes a plurality of teeth at said distal end for selectively engaging with said base about said slot.

25. A fascia clip as set forth in claim 23 wherein said gripping means wherein said gripping means includes a resilient tab and said distal end of said strap has an aperture receiving a distal end of said tab therein.

26. A fascia clip as set forth in claim 25 wherein said tab has a wedge-shaped tip projecting into said aperture of said strap.

27. A fascia clip as set forth in claim 23 wherein said base has an enlarged distal end and said gripping means includes a passage in said distal end of said base and a resilient tab projecting into said passage and wherein said strap has an aperture in said distal end thereof receiving said tab in resilient engagement.

28. A fascia clip as set forth in claim 27 wherein said base has a flat surface leading to said passage in angular relation to define a ramp for said distal end of said strap upon entry into said passage.

29. A fascia clip comprising
a base of elongated shape having a transverse opening at one end and gripping means including a slot at an opposite end; and
a flexible strap having a pointed distal end sized for passage through said opening of said base and for gripping in said slot of said gripping means and a proximal end of greater size than said opening, said strap including a plurality of teeth at said distal end for selectively engaging with said base about said slot.

30. A fascia clip comprising
a base of elongated shape having an opening at one end, gripping means at an opposite end and anchoring means for penetrating into fascia tissue intermediately of said ends; and
a flexible strap having a pointed distal end sized for passage through said opening of said base and for gripping in said gripping means and a proximal end of greater size than said opening.

31. A fascia clip comprising
a base of elongated shape having a first opening at a distal end and a second transverse opening at a proximal end; and
a resilient strap having a distal end sized for passage through said second opening an said first opening of said base, a proximal end of greater size than said second opening to prevent passage of said proximal end through said second opening and a plurality of teeth at said distal end of rengaging with said base to prevent withdrawal of said distal end of said strap from said first opening of said base.

32. A fascia clip comprising
a base of elongated shape having a main body portion, a pair of parallel flanges extending transversely of said main body portion at a distal end of said base and a web extending between and perpendicular to said flanges with a first opening therein and a proximal end extending angularly from said main body portion with a second opening therein;
a resilient strap having a distal end sized for passage through said second opening and said first opening of said base, a proximal end of greater size than said second opening to prevent passage of said proximal end through said second opening and means at said distal end for engaging with said base to prevent withdrawal of said distal end of said strap from said first opening of said base.

33. A fascia clip comprising
a base of elongated shape having an opening at one end;
a flexible strap having a pointed distal end sized for passage through said opening of said base and a proximal end of greater size than said opening; and
gripping means for gripping said distal end of said strap at said one end of said base, said gripping means including a slot in said base and a plurality of teeth on said strap for selectively engaging with said base about said slot.

34. A fascia clip comprising
a base of elongated shape having an opening at a proximal end, an enlarged distal end including a longitudinal passage and opening communicating transversely of said passage, and a resilient tab extending longitudinally of said opening and into said passage; and
a strap extending through said opening of said base and having a pointed distal end extending into said passage of said base, an enlarged proximal end seating against said base, and an aperture in said distal end receiving said tab to prevent withdrawal of said distal end of said strap from said passage of said base.

35. A fascia clip as set forth in claim 34 wherein said tab has a wedge-shaped tip extending into said aperture.

36. A fascia clip as set forth in claim 35 wherein said base and said strap are made of flexible absorbable material.

* * * * *